United States Patent
Tafesse

(10) Patent No.: US 10,550,090 B2
(45) Date of Patent: Feb. 4, 2020

(54) PROCESS FOR PREPARING SUBSTITUTED 9,10-DIOXO-9,10-DIHYDROANTHRECENES AND 6H-ANTHRA[1,9-CD]ISOXAZOL-6-ONES

(71) Applicant: Purdue Pharma L.P., Stamford, CT (US)

(72) Inventor: Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 16/085,829

(22) PCT Filed: Mar. 17, 2017

(86) PCT No.: PCT/US2017/022904
§ 371 (c)(1),
(2) Date: Sep. 17, 2018

(87) PCT Pub. No.: WO2017/161235
PCT Pub. Date: Sep. 21, 2017

(65) Prior Publication Data
US 2019/0084942 A1    Mar. 21, 2019

Related U.S. Application Data

(60) Provisional application No. 62/310,266, filed on Mar. 18, 2016.

(51) Int. Cl.
| | |
|---|---|
| *A61K 31/4965* | (2006.01) |
| *C07D 241/04* | (2006.01) |
| *C07C 227/18* | (2006.01) |
| *C07C 229/60* | (2006.01) |
| *C07D 413/04* | (2006.01) |

(52) U.S. Cl.
CPC .......... *C07D 241/04* (2013.01); *C07C 227/18* (2013.01); *C07C 229/60* (2013.01); *C07D 413/04* (2013.01)

(58) Field of Classification Search
CPC .............. A61K 31/4965; C07D 241/04; C07D 295/135
USPC .............. 514/255.03, 325; 544/381; 546/204
See application file for complete search history.

(56) References Cited

U.S. PATENT DOCUMENTS

| | | | |
|---|---|---|---|
| 9,040,508 | B2 | 5/2015 | Wu et al. |
| 2008/0139707 | A1 | 6/2008 | Kawakami et al. |
| 2015/0218132 | A1 | 8/2015 | Wu |
| 2017/0313666 | A1 | 11/2017 | Wu et al. |

FOREIGN PATENT DOCUMENTS

| | | |
|---|---|---|
| WO | WO-2010/077680 | 7/2010 |
| WO | WO-2017/027465 | 2/2017 |

OTHER PUBLICATIONS

Chang et al., "Human Health Effects of Sodium Azide Exposure: A Literature Review and Analysis" International Journal of Toxicology, 175-186 (2003).
Fulton et al., "The Use of Tosylhydrazone Salts as a safe Alternative for Handling Diazo Compounds and Their Applications in Organic Synthesis", 1479-1492, 2005.
International Search Report for International PCT Application No. PCT/US2017/022904 dated Mar. 17, 2017.
Pubchem; Substance Record for SID 236533848, Feb. 13, 2015, [retrieved on Feb. 5, 2017]. Retrieved from the internet . <URL: https://pubchem.ncbl.nlm.nib.gov/substance/236533648#section=Top>.
Wedlich, R.C., Reduce Thermal Risk in Industrial Synthesis, CEP Magazine, Oct. 2001, 60-65.

*Primary Examiner* — Jeffrey H Murray
(74) *Attorney, Agent, or Firm* — Purdue Pharma L.P.; Weiying Yang

(57) ABSTRACT

The disclosure provides processes of preparing compounds of Formula (I) and Formula (IV), their salts, and intermediates thereof, wherein $R^1$, $R^2$, $R^3$, and $R^7$ are defined as set forth in the specification.

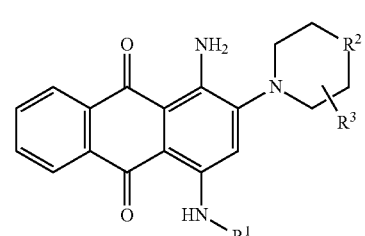

I

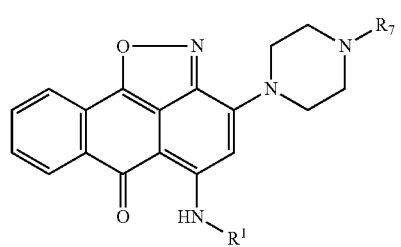

IV

19 Claims, No Drawings

PROCESS FOR PREPARING SUBSTITUTED 9,10-DIOXO-9,10-DIHYDROANTHRECENES AND 6H-ANTHRA[1,9-CD]ISOXAZOL-6-ONES

CROSS-REFERENCE TO RELATED APPLICATIONS

This application is a national stage application of PCT International Application Ser. No. PCT/US2017/022904, filed Mar. 17, 2017, designating the United States and published in English on Sep. 21, 2017 as publication WO 2017/161235 A1, which claims priority to U.S. Provisional Application Ser. No. 62/310,266, filed Mar. 18, 2016. The contents of the afore-mentioned patent applications are incorporated herein by their entirety.

FIELD OF THE INVENTION

The present disclosure relates to the process of preparing substituted heterocyclic compounds, and their salts, and intermediates thereof. In certain embodiments, the disclosure provides an improved synthesis of substituted 9,10-dioxo-9,10-dihydroanthrecene and 6H-anthra[1,9-cd]isoxazol-6-ones.

BACKGROUND

Certain substituted 9,10-dioxo-9,10-dihydroanthrecene and 6H-anthra[1,9-cd]isoxazol-6-one heterocyclic compounds of Formula I:

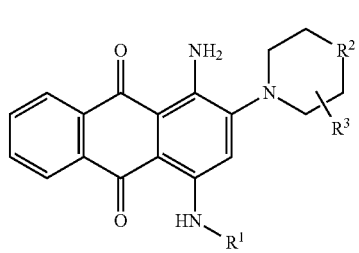

I and a process of preparing such compounds have been disclosed by Wu et al. (Wu et al., U.S. Publication No. 2015/0218132). A representative process for preparing compounds of Formula I, disclosed in Wu et al., is shown in Scheme 1:

Scheme 1

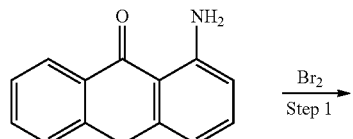

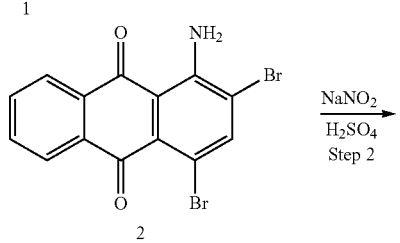

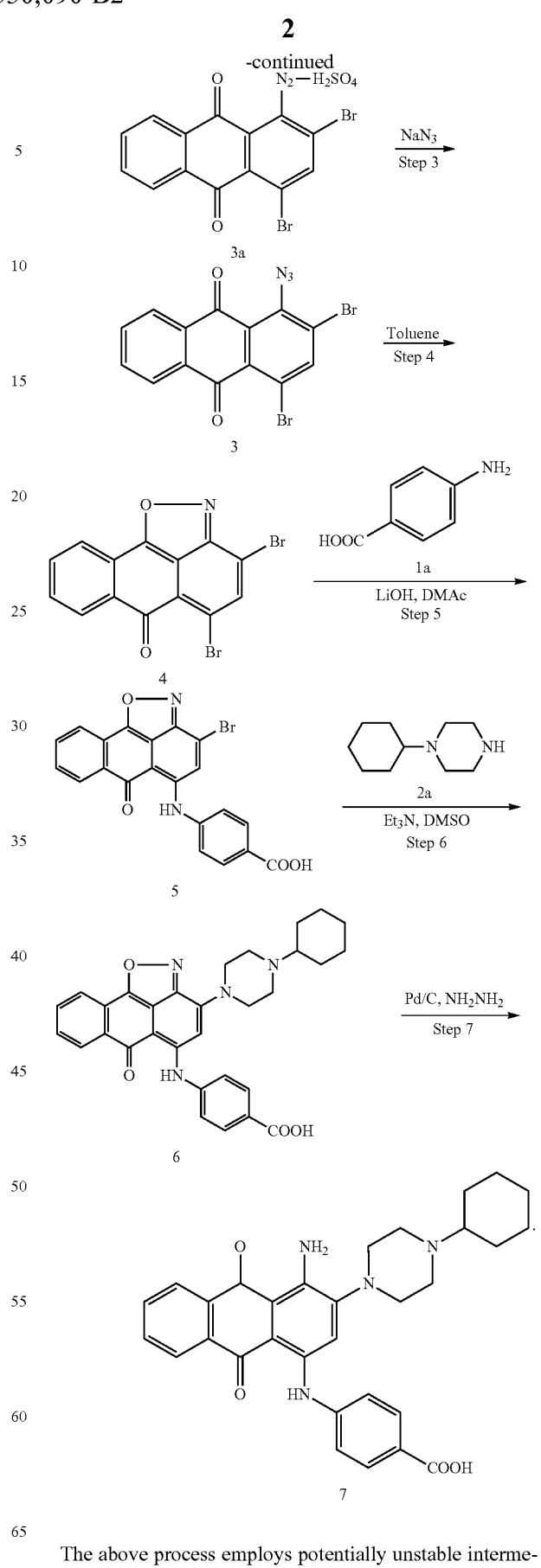

The above process employs potentially unstable intermediates that can undergo exothermic decompositions (compound 3a; Steps 2 and 3) (Wedlich, R. C., *Reduce Thermal Risk in Industrial Synthesis*, CEPMagazine, October 2001, 60-65 and Fulton, J. R. et al., *The Use of Tosylhydrazone Salts as a Safe Alternative for Handling Diazo Compounds and Their Application in Organic Synthesis*, Eur. J. Org. Chem. 1:1479-1492 (2005)), the use of sodium azide which is highly toxic and poisonous (Step 3) (Chang, S and Lamm, S. H., *Human Health Effects of Sodium Azide Exposure: A Literature Review and Analysis*, Int. J. of Toxicology, 22:175-186 (2003)), and the production of compounds that contain azide substituents which are also potentially toxic and poisonous (compound 3) (Chang et al.). The process also goes through seven steps to produce the desired product (See Scheme 1). The lengthy synthesis and the hazardous reaction conditions result in a process that is both inefficient from economic perspective and also potentially dangerous to whoever carry out the process.

Certain compounds of Formula IV:

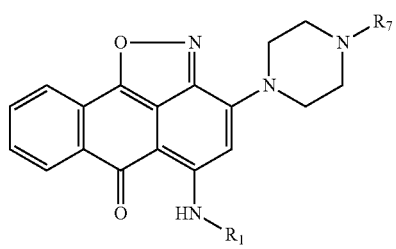

and a process of preparing such compounds were also disclosed by Wu et al. A representative process to synthesize compounds of Formula IV is shown in Scheme 1 (e.g., Compound 6 in Scheme 1) (see also Wu, U.S. Patent Publication 2015/0218132). Thus, the preparation of compounds of Formula IV is subject to the same disadvantages as the process for preparing compounds of Formula I.

It is also known that the compounds of Formula I and Formula IV can act as protein kinase inhibitors and/or antagonists. In particular, the compounds are described as Nerve Growth Factor (NGF) receptor Tyrosine receptor kinase A (TrkA) inhibitors and/or antagonists that can be used for the treatment and/or prevention of certain types of cancers, itching, atopic dermatitis, scabies, pityriasis, inflammation, restenosis, atherosclerosis, psoriasis, thrombosis, Alzheimer's, pain, a disease, disorder, injury, or malfunction relating to dysmyelination or demyelination or the disease or disorder associated with abnormal activities of protein kinases (Wu et al., WO 2010/077680, Wu et al., U.S. Pat. No. 9,040,508, and Wu et al., U.S. Publication No. 2015/0218132).

Thus, there is a need for technically simple and economic processes for the synthesis of the compounds of Formula I and Formula IV.

BRIEF SUMMARY OF THE INVENTION

An aspect of the present disclosure is directed to a process for preparing substituted 9,10-dioxo-9,10-dihydroanthrecenes of Formula I:

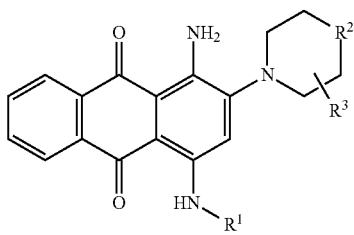

or a pharmaceutically acceptable salt thereof;
wherein:
$R^1$ is optionally substituted aryl group;
$R^2$ is $NR^7$ and $CR^9R^{10}$;
$R^3$, $R^9$, and $R^{10}$ are independently selected from the group consisting of hydrogen, halogen, CN, $NH_2$, $NO_2$, $C_{1-4}$ haloalkyl, $-O-C_{1-4}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-O-C_{6-10}$ aryl, $-O-C_{5-10}$ heterocycle, $-C(O)CF_3$, $-(CH_2)_n$halogen, $-(CHR)_n-(O)_n-C(=O)R^8$, $-(CHR)_n-(S)_n-C(=O)R^8$, $-OR^a$, $-NR^{11}R^{12}$, $-NR^aCOR^{11}$, $-NR^aCOOR^a$, $-NR^aSO_2R$, $-NR^aCONR^{11}R^{12}$, $-COR^a$, $-(CHR)_nCOOR^a$, $-S-C_{1-6}$ alkyl, and $CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^7$ is hydrogen, halogen, CN, $C_{1-4}$ haloalkyl, $-O-C_{1-4}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-C(O)CF_3$, $-(CH_2)_n$halogen, $-COR^a$, $-(CHR)nCOOR^a$, and $-CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^{11}$ and $R^{12}$ are independently selected from the group consisting of hydrogen, $N(R^a)C(=O)R$, halogen, CN, $NH_2$, $NHR^a$, $NO_2$, $C_{1-4}$ haloalkyl, $-O-C_{1-4}$ haloalkyl, $C_{1-6}$ alkyl, $C_{2-8}$ alkenyl, $-S-C_{1-6}$ alkyl, $-C(=O)-(O)_n-R^a$, $-(CHR)_n-(O)_n-C(=O)R^8$, $-(CHR)_n-(S)_n-C(=O)R^8$, $-OR^a$, $-(CHR)_nC_{3-10}$ cycloalkyl, $-(CHR)_nC_{6-10}$ aryl, $-(CHR)_nC_{6-10}$ heteroaryl, and $-(CHR)_nC_{5-10}$ heterocycle, wherein each said alkyl, alkenyl, cycloalkyl, aryl, heteroaryl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$, and wherein one or more carbon atoms of said alkyl may be replaced with one or more heteroatoms independently selected from the group consisting of nitrogen, oxygen, and sulfur; alternatively, $R^{11}$ and $R^{12}$, taken together with the atom(s) to which they are attached, form a 3 to 6 membered heterocyclic group containing one or more heteroatoms independently selected from the group consisting of nitrogen, oxygen, and sulfur; wherein the heterocyclic group is optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

R each independently represents hydrogen, halogen, CN, $NO_2$, $NH_2$, or $C_{1-6}$ alkyl;

$R^a$ ach independently represents hydrogen or $C_{1-6}$ alkyl;

$R^8$ each independently represents $C_{1-6}$ alkyl, halogen, CN, $NO_2$, $NH_2$, $NHR^a$, $SO_2R^{13}$, or $NR^aSO_2R^{13}$;

$R^{13}$ is hydrogen, $C_{1-6}$ alkyl, cycloalkyl, aryl, heteroaryl, or heterocycle; and n represents an integer from 0 to 3;
said process includes:
reacting a compound of Formula II:

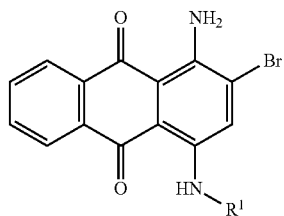

with

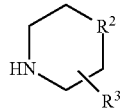

wherein:
$R^1$, $R^2$ and $R^3$ are defined as above;
to give said compound of Formula I.

Another aspect of the disclosure is drawn to a process of preparing a compound of Formula IV:

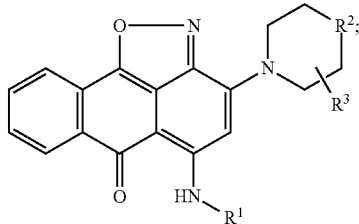

or a pharmaceutically acceptable salt thereof;
comprising subjecting a compound of Formula I:

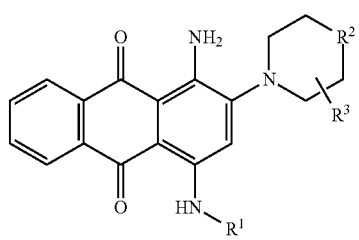

to intramolecular ring closing reaction conditions (for example, those described herein) that result in a compound of Formula IV,
wherein:
$R^1$, $R^2$, and $R^3$ are defined above.

In another aspect of the disclosure, novel compounds of Formula II are provided:

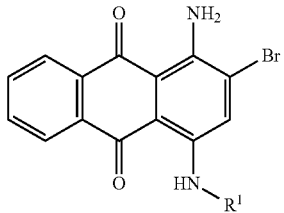

or salt thereof;
wherein:
$R^1$ is optionally substituted aryl group.
Suitable groups that can be used as $R^1$ include groups of the formula

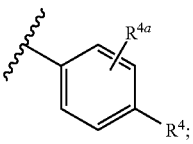

wherein:
$R^4$ is hydrogen, halogen, CN, $NO_2$, $CF_3$, —$(CHR)_nCOOR^{11}$, —$(CHR)_nSO_2R^{11}$, $C_{1-4}$ haloalkyl, —$OC_{1-4}$-haloalkyl, $C_{2-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —O—$C_{6-10}$ aryl, —O—$C_{5-10}$ heterocycle, —$(CHR)_nC(O)CF_3$, —$(CHR)_nC(OH)(CF_3)_2$, —$(CH_2)_n$halogen, —$OR^{16}$, —$NR^{11}R^{12}$, —$NR^aCOR^{11}$, —$NR^aCOOR^{11}$, —$NR^aSO_2R^{11}$, —$NR^aCONR^{11}R^{12}$, —$COR^{11}$, tetrazole, —$(CHR)_n$tetrazole, —S—$C_{1-6}$ alkyl, or —$CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^{4a}$ is independently selected from the group consisting of hydrogen, halogen, CN, $NH_2$, $NO_2$, $C_{1-4}$ haloalkyl, —$OC_{1-4}$ haloalkyl, $C_{1-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —O—$C_{6-10}$ aryl, —O—$C_{5-10}$ heterocycle, —$C(O)CF_3$, —$(CH_2)$nhalogen, —(CHR), —$(O)_n$—$C(=O)R^8$, —$(CHR)_n$—$(S)_n$—$C(=O)R^8$, —$OR^a$, —$NR^{11}R^{12}$, —$NR^aCOR^{11}$, —$NR^aCOOR^a$, —$NR^aSO_2R$, —$NR^aCONR^{11}R^{12}$, —$COR^a$, —$(CHR)_nCOOR^a$, —S—$C_{1-6}$ alkyl, and —$CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^{11}$ and $R^{12}$ are independently selected from the group consisting of hydrogen, $N(R^a)C(=O)R$, halogen, CN, $NH_2$, $NHR^a$, $NO_2$, $C_{1-4}$ haloalkyl, —$OC_{1-4}$ haloalkyl, $C_{1-6}$ alkyl, $C_{2-8}$ alkenyl, —S—$C_{1-6}$ alkyl, —$C(=O)$—$(O)_n$—$R^a$, —$(CHR)_n$—$(O)_n$—$C(=O)R^8$, —$(CHR)_n$—$(S)_n$—$C(=O)$ $R^8$, —$OR^a$, —$(CHR)_nC_{3-10}$ cycloalkyl, —$(CHR)_nC_{6-10}$ aryl, —$(CHR)_nC_{5-10}$ heteroaryl, and —$(CHR)_nC_{5-10}$ heterocycle, wherein each said alkyl, alkenyl, cycloalkyl, aryl, heteroaryl and heterocycle is independently optionally substituted with 1 to 2 groups of $R^8$, and wherein one or more carbon atoms of said alkyl may be replaced with one or more heteroatoms independently selected from the group consisting of nitrogen, oxygen, and sulfur; alternatively, $R^{11}$ and $R^{12}$, taken together with the atom(s) to which they are attached, form a 3 to 6 membered heterocyclic group containing one or more heteroatoms independently selected from the group consisting of nitrogen, oxygen, and sulfur; wherein the heterocyclic group is optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$; and R each independently represents hydrogen, halogen, CN, $NO_2$, $NH_2$, or $C_{1-6}$ alkyl;

$R^a$ each independently represents hydrogen or $C_{1-6}$ alkyl;

$R^8$ each independently represents $C_{1-6}$ alkyl, halogen, CN, $NO_2$, $NH_2$, $NHR^a$, $SO_2R^{13}$, or $NR^aSO_2R^{13}$;

$R^{13}$ is hydrogen, $C_{1-6}$ alkyl, cycloalkyl, aryl, heteroaryl, or heterocycle;

$R^{16}$ is hydrogen, halogen, CN, $C_{1-4}$ haloalkyl, $C_{1-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —$C(O)CF_3$, —$(CH_2)_n$halogen, —$COR^a$, —$(CHR)_nCOOR^a$, —S—$C_{1-6}$ alkyl, and —$CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$; and n represents an integer from 0 to 3;

and wherein if $R^{4a}$ is hydrogen, then $R^4$ is not hydrogen, halogen, $CH_3$, $CF_3$, $OCH_3$, CN, $NO_2$, $CF_3$, COOH, —O—$C_{6-10}$ aryl.

Compounds of Formula I and Formula IV are capable of inhibiting or antagonizing protein kinase activities. The compounds can be used for the treatment and/or prevention of certain types of cancers, itching, atopic dermatitis, scabies, pityriasis, inflammation, restenosis, atherosclerosis, psoriasis, thrombosis, Alzheimer's, pain, a disease, disorder, injury, or malfunction relating to dysmyelination or demyelination or the disease or disorder associated with abnormal activities of protein kinases.

DETAILED DESCRIPTION OF THE INVENTION

The present disclosure provides novel processes of preparing compounds of Formula I, Formula IV, their salts, and intermediates thereof. Certain compounds prepared by the processes of the invention are useful as protein kinase inhibitors and/or antagonists that can be used for the treatment and/or prevention of certain types of cancers, itching, atopic dermatitis, scabies, pityriasis, inflammation, restenosis, atherosclerosis, psoriasis, thrombosis, Alzheimer's, pain, a disease, disorder, injury, or malfunction relating to dysmyelination or demyelination or the disease or disorder associated with abnormal activities of protein kinases.

One aspect of the disclosure is drawn to a process of preparing compounds of Formula I, or pharmaceutically acceptable salt(s) thereof, described below:

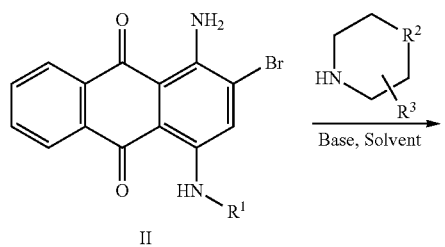

-continued

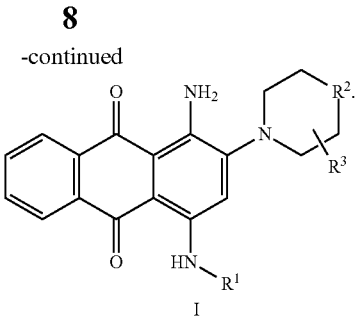

In this aspect, certain embodiments provide a process of forming the compound of Formula I starting from a compound of Formula II, which can be carried out at a suitable temperature and pressure. In one embodiment, the suitable temperature is from about 100° C. to about 140° C., from about 110° C. to about 130° C., or from about 120° C. to about 125° C.

The reaction to form the compound of Formula I starting from a compound of Formula II can be carried out in a polar, aprotic solvent. In one embodiment, the solvent is DMSO or DMF. In a certain embodiment, the solvent is DMSO.

In one embodiment, the reaction time (e.g., a time duration for the reaction to be considered as substantially complete) is from about 4 hours to about 12 hours, about 6 hours to about 10 hours, or about 8 hours.

The reaction to form the compound of Formula I starting from a compound of Formula II can take place in the presence of a base, which can be either an organic base or an inorganic base. In one embodiment, the base is triethyl amine or diisopropyl amine. In a certain embodiment, the base is triethyl amine.

Another aspect of the disclosure is directed to a process for preparing a substituted heterocyclic compound of Formula IV, or pharmaceutically acceptable salt(s) thereof, as described above. In this aspect, certain embodiments of the process comprise a step of forming the compound of Formula V:

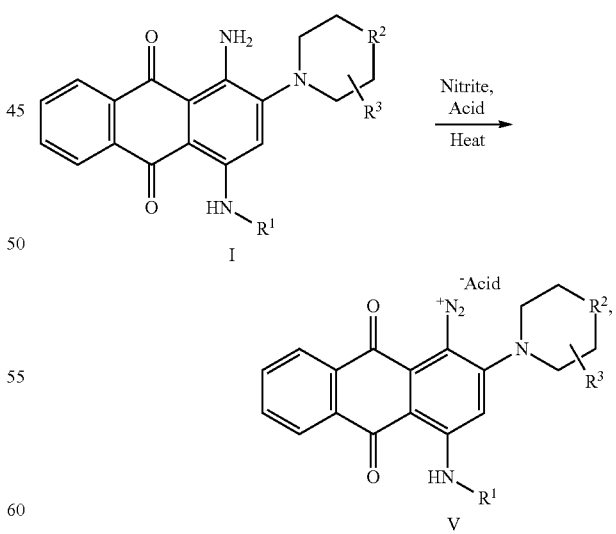

which takes place in the presence of a nitrite and an acid. In one embodiment, the nitrite and the acid are sodium nitrite and sulfuric acid, respectively. Other useful acids include hydrochloric acid (HCl), p-toluenesulfonic acid (pTsOH), or tetrafluoroboric acid ($HBF_4$).

In one embodiment, the reaction temperatures to form the compound of Formula V starting from a compound of Formula I are from about 35° C. to about 75°, from about 45° C. to about 65° C., or about 55° C.

In one embodiment, the reaction time to form the compound of Formula V starting from a compound of Formula I is from about 2 hours to about 8 hours, about 3 hours to about 6 hours, or about 4 hours.

In one embodiment, the process of forming the compound of Formula IV further comprises the following reaction:

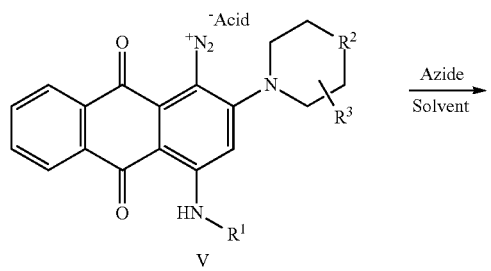

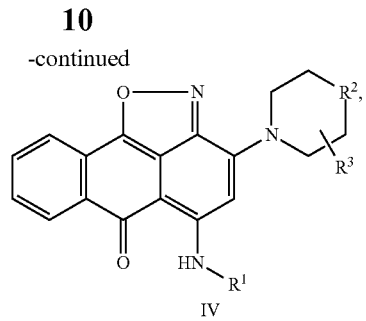

which takes place in the presence of a solvent and under heat. In one embodiment the solvent is toluene. Other useful solvents include DMF, DMSO, and NMP.

In one embodiment the reaction temperatures to form the azide intermediate of Formula VI are from about 50° C. to about 90°, from about 60° C. to about 80° C., or about 70° C.

In one embodiment the reaction time to form the azide intermediate of Formula VI is from about 6 hours to about 18 hours, about 8 hours to about 16 hours, about 10 hours to about 14 hours, or about 12 hours.

Another aspect of the disclosure is directed to a process of preparing a compound of Formula II:

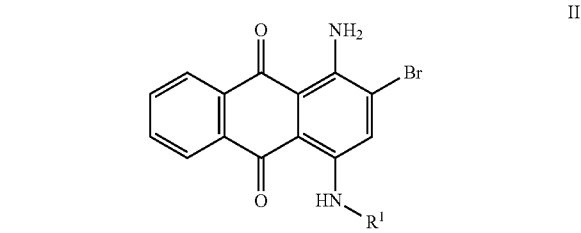

wherein the reaction takes place in the presence of an azide and solvent. In one embodiment the azide and solvent are sodium azide and water, respectively. Other useful solvents include water, acetic acid or mixtures of water and acetic acid.

In one embodiment, the reaction temperatures to form the compound of Formula VI starting from a compound of Formula V are from about 10° C. to about 40°, from about 20° C. to about 30° C., or about room temperature.

In one embodiment, the reaction time to form the compound of Formula VI starting from a compound of Formula V is from about 6 hours to about 18 hours, about 8 hours to about 16 hours, about 10 hours to about 14 hours, or about 12 hours.

In one embodiment, the process of forming the compound of Formula IV comprises the following reaction:

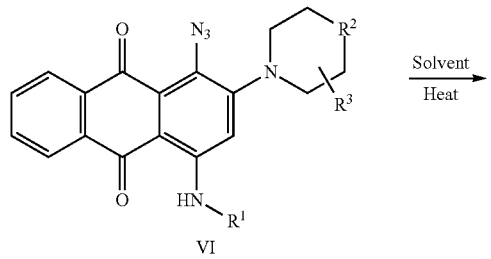

comprising reacting a compound of formula III:

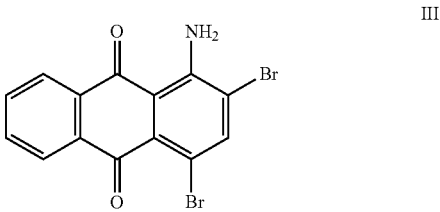 [SMILES: Nc1c(Br)cc(Br)c2c1C(=O)c1ccccc1C2=O]

with $H_2NR^1$,
wherein:
$R^1$ is an optionally substituted aryl group.

The process of forming the compound of Formula II starting from a compound of Formula III can be carried out at a suitable temperature and pressure. In one embodiment, the reaction temperature to form compounds of Formula II is from about 95° C. to about 165° C., from about 105° C. to about 155° C., from about 115° C. to about 145° C., or from about 125° C. to about 135° C.

The reaction to form the compound of Formula II starting from a compound of Formula III can be carried out in an alcohol. In one embodiment of the reaction, the alcohol is cyclohexyl alcohol.

In one embodiment, the reaction time is form about 4 hours to about 12 hours, from about 6 hours to about 10, or about 8 hours.

The reaction to form the compound of Formula II starting from a compound of Formula III can take place in the presence of copper (II) acetate, copper metal, and potassium acetate.

For each of the above formulae that includes $R^1$, suitable $R^1$ groups include those of the following formula:

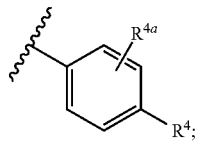

wherein $R^4$ is hydrogen, halogen, CN, $NO_2$, $CF_3$, $-(CHR)_nCOOR^{11}$, $-(CHR)_nSO_2R^{11}$, $C_{1-4}$ haloalkyl, $-OC_{1-4}$-haloalkyl, $C_{2-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-O-C_{6-10}$ aryl, $-O-C_{5-10}$ heterocycle, $-(CHR)_nC(O)CF_3$, $-(CHR)_nC(OH)(CF_3)_2$, $-(CH_2)_n$halogen, $-OR^{16}$, $-NR^{11}R^{12}$, $-NR^aCOR^{11}$, $-NR^aCOOR^{11}$, $-NR^aSO_2R^{11}$, $-NR^aCONR^{11}R^{12}$, tetrazole, $-(CHR)_n$tetrazole, $-S-C_{1-6}$ alkyl, or $-CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^{4a}$ is independently selected from the group consisting of hydrogen, halogen, CN, $NH_2$, $NO_2$, $C_{1-4}$ haloalkyl, $-OC_{14}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-O-C_{6-10}$ aryl, $-O-C_{5-10}$ heterocycle, $-C(O)CF_3$, $-(CH_2)_n$halogen, $-(CHR)_n-(O)_n-C(=O)R^8$, $-(CHR)_n-(S)_n-C(=O)R^8$, $-OR^a$, $-NR^{11}R^{12}$, $-NR^aCOR^{11}$, $-NR^aCOOR^a$, $-NR^aSO_2R$, $-NR^aCONR^{11}R^{12}$, $-COR^a$, $-(CHR)_nCOOR^a$, $-S-C_{1-6}$ alkyl, and $-CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^7$ is hydrogen, halogen, CN, $C_{1-4}$ haloalkyl, $-OC_{1-4}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-C(O)CF_3$, $-(CH_2)_n$halogen, $-COR^a$, $-(CHR)_nCOOR^a$, and $-CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^{11}$ and $R^{12}$ are independently selected from the group consisting of hydrogen, $N(R^a)C(=O)R$, halogen, CN, $NH_2$, $NHR^a$, $NO_2$, $C_{1-4}$ haloalkyl, $-OC_{1-4}$ haloalkyl, $C_{1-6}$ alkyl, $C_{2-8}$ alkenyl, $-S-C_{1-6}$ alkyl, $-C(=O)-(O)_n-R^a$, $-(CHR)_n-(O)_n-C(=O)R^8$, $-(CHR)_n-(S)_n-C(=O)R^8$, $-OR^a$, $-(CHR)_nC_{3-10}$ cycloalkyl, $-(CHR)_nC_{6-10}$ aryl, $-(CHR)_nC_{5-10}$ heteroaryl, and $-(CHR)_nC_{5-10}$ heterocycle, wherein each said alkyl, alkenyl, cycloalkyl, aryl, heteroaryl and heterocycle is independently optionally substituted with 1 to 2 groups selected from $C_{1-6}$ alkyl, halogen, CN, $NO_2$, $NH_2$, $NHR^a$, $SO_2R^{13}$, or $NR^aSO_2R^{13}$, and wherein one or more carbon atoms of said alkyl may be replaced with one or more heteroatoms selected from the group consisting of nitrogen, oxygen, and sulfur; alternatively, $R^{11}$ and $R^{12}$, taken together with the atom(s) to which they are attached, form a 3 to 6 membered heterocyclic group containing one or more heteroatoms independently selected from the group consisting of nitrogen, oxygen, and sulfur; wherein the heterocyclic group is optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$; and R each independently represents hydrogen, halogen, CN, $NO_2$, $NH_2$, or $C_{1-6}$ alkyl;

$R^a$ each independently represents hydrogen or $C_{1-6}$ alkyl;

$R^8$ each independently represents $C_{1-6}$ alkyl, halogen, CN, $NO_2$, $NH_2$, $NHR^a$, $SO_2R^{13}$, or $NR^aSO_2R^{13}$;

$R^{13}$ is hydrogen, $C_{1-6}$ alkyl, cycloalkyl, aryl, heteroaryl, or heterocycle;

$R^{16}$ is hydrogen, halogen, CN, $C_{1-4}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-C(O)CF_3$, $-(CH_2)_n$halogen, $-COR^a$, $-(CHR)nCOOR^a$, $-S-C_{1-6}$ alkyl, and $-CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$; and n represents an integer from 0 to 3.

A certain embodiment of the above formulae provides:

$R^2$ is $NR^7$;

$R^3$ is H;

$R^7$ is independently selected from the group consisting of hydrogen, halogen, CN, $C_{1-4}$ haloalkyl, $-OC_{1-4}$ haloalkyl, $C_{1-6}$ alkyl, $C_{2-6}$ alkenyl, $C_{2-6}$ alkynyl, $-(CHR)_nC_{6-10}$ aryl, $-(CHR)_nC_{5-8}$ heterocycle, $-(CHR)_nC_{3-8}$ cycloalkyl, $-C(O)CF_3$, $-(CH_2)_n$halogen, $-COR^a$, $-(CHR)nCOOR^a$, and $CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

$R^{11}$ and $R^{12}$ are independently selected from the group consisting of hydrogen, $N(R^a)C(=O)R$, halogen, CN, $NH_2$, $NHR^a$, $NO_2$, $C_{1-4}$ haloalkyl, $-OC_{1-4}$ haloalkyl, $C_{1-6}$ alkyl, $C_{2-8}$ alkenyl, $-S-C_{1-6}$ alkyl, $-C(=O)-(O)_n-R^a$, $-(CHR)_n-(O)_n-C(=O)R^8$, $-(CHR)_n-(S)_n-C(=O)R^8$, $-OR^a$, $-(CHR)_nC_{3-10}$ cycloalkyl, $-(CHR)_nC_{6-10}$ aryl, $-(CHR)_nC_{5-10}$ heteroaryl, and $-(CHR)_nC_{5-10}$ heterocycle, wherein each said alkyl, alkenyl, cycloalkyl, aryl, heteroaryl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$, and wherein one or more carbon atoms of said alkyl may be replaced with one or more heteroatoms selected from the group consisting of nitrogen, oxygen, and sulfur; alternatively, $R^{11}$ and $R^{12}$, taken together with the atom(s) to which they are attached, form a 3 to 6 membered heterocyclic group containing one or more heteroatoms independently selected from the group consisting of nitrogen, oxygen, and sulfur; wherein the heterocyclic group is optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

R each independently represents hydrogen, halogen, CN, $NO_2$, $NH_2$, or $C_{1-6}$ alkyl;

$R^a$ each independently represents hydrogen or $C_{1-6}$ alkyl;

$R^8$ each independently represents $C_{1-6}$ alkyl, halogen, CN, $NO_2$, $NH_2$, $NHR^a$, $SO_2R^{13}$, or $NR^aSO_2R^{13}$;

$R^{13}$ is hydrogen, $C_{1-6}$ alkyl, cycloalkyl, aryl, heteroaryl, or heterocycle; and n represents an integer from 0 to 3.

One embodiment of the above formulae provides $R^1$ is

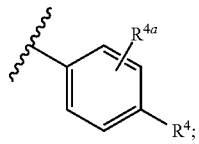

$R^4$ is COOH;
$R^{4a}$ is hydrogen;
$R^2$ is $NR^7$;
$R^3$ is H; and
$R^7$ is cyclohexyl.

Terms used in the claims and specification are defined as set forth below unless otherwise specified.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tent-butyl, iso-butyl, 3-pentyl, hexyl, heptyl, octyl, nonyl, and decyl. Non-limiting exemplary $C_{1-4}$ alkyl groups include methyl, ethyl, propyl, iso-propyl, butyl, sec-butyl, tent-butyl, and iso-butyl.

In the present disclosure, the term "alkenyl" as used by itself or as part of another group refers to an alkyl containing one, two or three carbon-to-carbon double bonds. In one embodiment, the alkenyl has one carbon-to-carbon double bond. In another embodiment, the alkenyl is a $C_{2-6}$ alkenyl. In another embodiment, the alkenyl is a $C_{2-4}$ alkenyl. Non-limiting exemplary alkenyl groups include ethenyl, propenyl, isopropenyl, butenyl, sec-butenyl, pentenyl, and hexenyl.

In the present disclosure, the term "alkynyl" as used by itself or as part of another group refers to an alkyl containing one to three carbon-to-carbon triple bonds. In one embodiment, the alkynyl has one carbon-to-carbon triple bond. In another embodiment, the alkynyl is a $C_{2-6}$ alkynyl. In another embodiment, the alkynyl is a $C_{2-4}$ alkynyl. Non-limiting exemplary alkynyl groups include ethynyl, propynyl, butynyl, 2-butynyl, pentynyl, and hexynyl groups.

In the present disclosure, the term "alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is $(C_1$-$C_{20})$ alkyldiyl, more preferably, $(C_1$-$C_{10})$ alkyldiyl, most preferably, $(C_1$-$C_6)$ alkyldiyl.

In the present disclosure, the term "alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used.

In the present disclosure, the term "acyl" by itself or as part of another substituent refers to a radical —$C(O)R^{14}$, where $R^{14}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl.

In the present disclosure, the term "amino" by itself or as part of another substituent refers to a radical —$NR^aR^b$, where $R^a$ and $R^b$ are independently hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein, or alternatively $R^a$ and $R^b$, taken together with the atoms to which they are bonded, form a cycloheteroalkyl ring. Representative examples include, but are not limited to —$NH_2$, —$NHCH_3$, —$N(CH_3)_2$, —NH-phenyl, —NH—$CH_2$-phenyl, pyrrolidine.

In the present disclosure, the term "aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

In the present disclosure, the term "arylalkyl," or "aralkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenyl ethan-1 2-phenyl ethen-1-naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl. In the present disclosure, the term "aryloxy," by itself or as part of another substituent, refers to a radical of the formula —O—$R^{15}$, where $R^{15}$ is aryl, substituted aryl, arylalkyl, or substituted arylalkyl.

In the present disclosure, the term "aryloxycarbonyl," by itself or as part of another substituent, refers to a radical of the formula —C(O)—O—$R^{15}$, where $R^{15}$ is aryl, substituted aryl, arylalkyl, or substituted arylalkyl.

In the present disclosure, the term "cycloalkyl" or "carbocyclyl" by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, a cycloalkyl group comprises from 3 to 10 ring atoms ($C_3$-$C_{10}$ cycloalkyl). In other embodiments, a cycloalkyl group comprises from 3 to 7 ring atoms ($C_3$-$C_7$ cycloalkyl). The term "heterocyclic" or "heterocyclyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, B, N, P, O, S, Si, etc.

In the present disclosure, the term "halogen" or "halo" by itself or as part of another substituent, refers to any of the elements fluorine, chlorine, bromine, iodine, and astatine, occupying group VIIA (17) of the periodic table.

In the present disclosure, the term "heteroaryl" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is selected from the group consisting of thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In the present disclosure, the term "substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halogen, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, substituted alkyl, arylalkyl, alkyldiyl, substituted alkyldiyl, aryl, substituted aryl, arylalkyl, substituted arylalkyl, heteroalkyl, substituted heteroalkyl, heteroalkyldiyl, substituted heteroalkyldiyl, heteroaryl, substituted heteroaryl, heteroarylalkyl substituted heteroarylalkyl; each $R^b$ is independently hydrogen or $R^a$; and each $R^c$ is independently $R^b$ or alternatively, the two $R^c$s are taken together with the nitrogen atom to which they are bonded form a cycloheteroalkyl ring which may optionally include from 1 to 4 of the same or different additional heteroatoms selected from the group consisting of O, N and S. As specific examples, —$NR^cR^c$ is meant to include —NH$_2$, —NH-alkyl, N-pyrrolidinyl and N-morpholinyl. In the present disclosure, an "polypeptide" and "protein" are used interchangeably herein to refer a polymer of amino acids, and unless otherwise limited, include atypical amino acids that can function in a similar manner to naturally occurring amino acids.

In the present disclosure, an "inhibitor" or "antagonist" of a polypeptide is an agent that reduces, by any mechanism, any action or function of the polypeptide, as compared to that observed in the absence (or presence of a smaller amount) of the agent. An inhibitor of a polypeptide can affect: (1) the expression, mRNA stability, protein trafficking, modification (e.g., phosphorylation), or degradation of a polypeptide, or (2) one or more of the normal action or functions of the polypeptide. An inhibitor of a polypeptide can be non-selective or selective. Preferred inhibitors (antagonists) are generally small molecules that act directly on, and are selective for, the target polypeptide.

In the present disclosure, the term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

In the present disclosure, the term "reaction time" refers to 1) a time duration for a reaction to be considered as substantially complete, according to analytical measurements (e.g., mass spectrum, NMR, and HPLC); or 2) a time duration for the reaction, after which no noticeable or significant progress to a desired product is observed (such as, at the time when chemical equilibrium is reached): or 3) an optimal time duration for the reaction, after which the longer the reaction takes place, the more disadvantages it brings to final results (such as, more side products. or worse yields of the desired final products). It is well understood in the chemical arts that the reaction time is in part a result of reaction kinetics of chemical processes.

In the present disclosure, the term "treating", "treat" or "treatment" of any disease or disorder refers, in some embodiments, to ameliorating or preventing the disease or disorder (i.e., arresting, preventing, holding or reducing the development of the disease or at least one of the clinical symptoms thereof). In other embodiments "treating", "treat" or "treatment" refers to ameliorating at least one physical parameter, which may not be discernible by the patient. In yet other embodiments, "treating", "treat" or "treatment" refers to inhibiting, or holding or preventing the progress of, the disease or disorder, either physically, (e.g., stabilization of a discernible symptom), physiologically, (e.g., stabilization of a physical parameter) or both. In yet other embodiments, "treating", "treat" or "treatment" refers to delaying the onset of the disease or disorder.

In the present disclosure, the term "therapeutically effective amount" means the amount of a compound that, when administered to a patient for treating a disease, is sufficient to affect such treatment for the disease. The "therapeutically effective amount" will vary depending on the compound, the disease and its severity and the age, weight, etc., of the patient to be treated. The present disclosure encompasses the preparation and use of salts of the compounds prepared by the disclosed method. As used herein, the pharmaceutical "pharmaceutically acceptable salt" refers to salts or zwitterionic forms of Compounds of Formula I and Formula IV. Salts of Compounds of the Disclosure can be prepared during the final isolation and purification of the compounds or separately by reacting the compound with an acid having a suitable cation. The pharmaceutically acceptable salts of Compounds of Formula I and Formula IV can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. Another aspect of the disclosure encompasses is the use of a compound prepared by the disclosed method, and its salts thereof, as protein kinase inhibitor and/or antagonists, particular as NGF receptor TrkA inhibitor and/or antagonist for the preparation of a medicament for the treatment and/or prevention of diseases associated directly or indirectly with inhibiting TrkA, which including certain cancer (e.g., pancreatic cancer, gastric cancer, esophageal cancer, gastrointestinal cancer, colorectal cancer, lung (small cell and non-small cell) cancer, liver cancer, hepatocellular carcinoma, intrahepatic cholangiocarcinoma, brain cancer or human neuroblastoma, glioblastoma and medulloblastoma, retinoblastoma, leukemia, lymphoma, melanoma, malignant mesothelioma, breast cancer, bladder cancer, ovarian cancer, prostate cancer or metastasis, thyroid cancer, squamous cell carcinomas, spitz tumors, spitzoid melanomas, acute myelogenous leukemia, endometrial cancer, skin cancer, oral cancer, bone cancer, melanoma), itching, atopic dermatitis, scabies, pityriasis, inflammatory bowel disease, inflammatory arthritis, asthma, human airway diseases, respiratory disease, fibrotic disease, renal fibrosis, liver fibrosis, liver cirrhosis, restenosis, atherosclerosis, psoriasis, thrombosis, Chagas' disease, parasitic diseases, Alzheimer's, pain (i.e, reducing pain for a subject in need thereof, including acute pain, chronic pain, inflammatory pain, neuropathic pain, cancer pain, and generalized pain disorder), Pulmonary Inflammatory Diseases, pulmonary sarcoidosis, bladder dysfunction or lower urinary tract dysfunction, Paget's disease, diabetic nephropathy, irritable bowel syndrome, radiation, schizophrenia, a disease, disorder, injury, or malfunction relating to dysmyelination or demyelination or the disease or disorder associated with abnormal activities of protein kinases.

When administered to a patient, compounds of Formula I and Formula IV prepared by the disclosed method can be administered as a component of a composition that comprises a pharmaceutically acceptable carrier or excipient. A compound prepared by the disclosed method can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a compound prepared by the disclosed method into the bloodstream.

Pharmaceutical compositions of the disclosure can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sub-lingual tablets or tabs, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in *Remington Pharmaceutical Sciences* 1447-1676 (Alfonso R. Gennaro ed., 19th ed. 1995), incorporated herein by reference.

Pharmaceutical compositions of the disclosure comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when a compound prepared by the disclosed method is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

The use of the terms "a", "an", "the", and similar referents in the context of this disclosure (especially in the context of the claims) are to be construed to cover both the singular and the plural, unless otherwise indicated. Recitation of ranges of values herein are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

In one embodiment, the disclosure provides a process illustrated by Scheme (2):

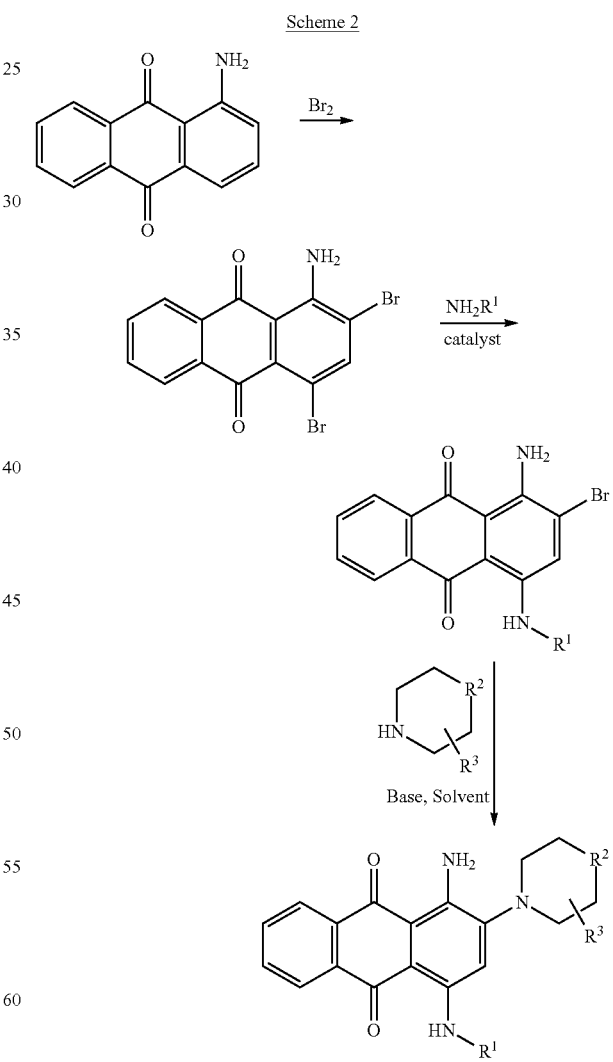

Scheme 2

In another embodiment, a process according to the disclosure is illustrated by Scheme (3) and examples that follow:

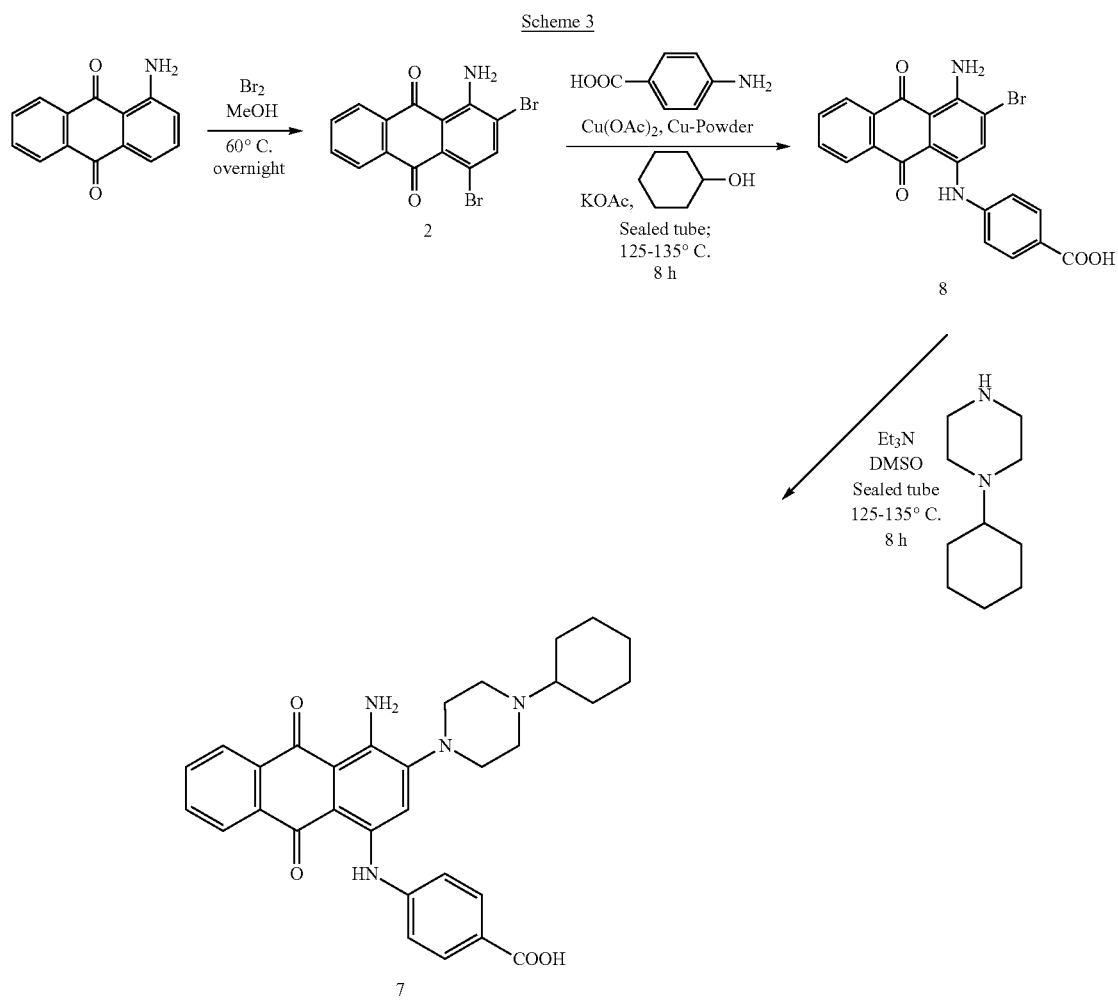

Scheme 3

ABBREVIATIONS

The following abbreviations are used in the present disclosure:

° C. Celsius degrees
Cu copper
Cu(OAc)$_2$ copper(II) acetate
DMF Dimethylformamide
DMSO dimethylsulfoxide
h hour(s)
HCl hydrochloric acid
HPLC high pressure liquid chromatography
KOAc potassium acetate
MeOH methanol
min minute(s)
MS mass spectrum
MTBE methyl t-butyl ether
NMP N-Methyl-2-pyrrolidone
NMR nuclear magnetic resonance
P$_2$O$_5$ phosphorus pentoxide

EXAMPLES

Example 1

Preparation of 1-amino-2,4-dibromoanthraquinone (Compound 2)

1-Aminoanthraquinone 1 (10 g, 1 eq, 44.8 mmol) was suspended in 250 mL of dry MeOH in a 500 mL three neck-round-bottom flask that was equipped with a mechanical stirrer and an addition funnel. Bromine (17.92 g, 2.5 eq, 112 mmol) was added dropwise at 60° C. to this suspension with vigorous stirring. The reaction mixture was stirred at 50-60° C. overnight (~17 h). Product formation was confirmed by MS analysis. The reaction was allowed to come to attain ambient temperature and the mixture was filtered through a sintered funnel, washed with methyl t-butyl ether (MTBE, 250 mL), and dried in air to give Compound 2 (15 g, 88% yield) as a bright red solid. $^1$H NMR (300 MHz, CDCl3) δ 8.19-8.27 (m, 2H), 8.07 (s, 1H), 7.71-7.78 (m, 2H).; m/z [negative ion]=378.9, 380.9, 382.9.

Example 2

Preparation of 3-((4-amino-3-bromo-9,10-dioxo-9,10-dihydroanthracen-1-yl)amino) benzoic acid (Compound 8)

In a 500 mL pressure bottle 1-amino-2,4-dibromoanthraquinone (Compound 2) (7.5 g, 1 eq, 19.7 mmol), 4-amino benzoic acid (32.32 g, 12 eq, 236.2 mmol), copper(II) acetate (1.06 g, 0.3 eq, 5.9 mmol), copper dust (0.38 g, 0.3 eq, 5.9 mmol) and potassium acetate (8.1 g, 4.2 eq, 82.5 mmol) were suspended with 150 mL of cyclohexanol under a nitrogen atmosphere. The pressure bottle was sealed and heated at 125-135° C. for 8 h. After reaction was complete (MS analysis), the mixture was cooled to ambient temperature. Ethanol (200 mL) was then added with vigorous stirring. The resulting precipitate was filtered off, washed with 250 mL of ethanol and dried under vacuum. The precipitate was treated with 175 mL of 1N HCl at 80-90° C. for 30 min, cooled to ambient temperature, and filtered. The solid product obtained was dried in a vacuum oven over $P_2O_5$ to give the desired Compound 8 (6.26 g, yield 73%) as a dark blue solid. $^1$H NMR (300 MHz, d6-DMSO) δ 11.65 (s, 1H), 8.18-8.30 (m, 2H), 8.02 (s, 1H), 7.95 (d, J=8.5 Hz, 2H), 7.92-7.85 (m, 2H), 7.38 (d, J=8.5 Hz, 2H).; m/z [negative ion]=436, 438.

Example 3

Preparation of 4-((4-amino-3-(4-cyclohexylpiperazin-1-yl)-9,10-dioxo-9,10-dihydroanthracen-1-yl)amino)benzoic acid (Compound 7)

In a 300 mL pressure bottle was added 3-((4-amino-3-bromo-9,10-dioxo-9,10-dihydroanthracen-1-yl)amino) benzoic acid (Compound 3) (6.25 g, 1 eq, 14.3 mmol), 1-cyclohexyl piperizine (4.57 g, 1.9 eq, 27.2 mmol), and triethylamine (4.2 mL, 2.1 eq, 30.0 mmol). To this was then added 75 mL of dry DMSO under nitrogen atmosphere. The pressure bottle was then sealed and heated at 120-125° C. for 8 h. After the reaction was complete (MS analysis), the mixture was cooled to ambient temperature. The dark blue reaction mixture was then poured into 700 mL of a 10:1 methyl t-butyl ether (MTBE): methanol solution and cooled in an ice bath for 30 min. The solid was filtered off and dried under vacuum to afford crude TK-384 (4.9 g). Purification by flash chromatography (in several batches due to poor solubility) eluting with methanol in dichloromethane (0-10%) provided Compound 7 (1.9 g, yield 25%) as a dark blue solid. $^1$H NMR (300 MHz, d6-DMSO) δ 12.9-12.5 (br s, 1H), 12.34 (s, 1H), 8.32-8.18 (m, 2H), 7.95 (d, J=8.6 Hz, 2H), 7.90-7.76 (m, 2H), 7.43 (d, J=8.6 Hz, 2H), 7.25 (s, 1H), 3.15-2.88 (br s, 4H), 2.88-2.60 (br s, 4H), 2.34-2.22 (m, 1H), 2.0-1.65 (m, 3H), 1.60-1.50 (m, 2H), 1.35-1.0 (m, 5H).; HPLC purity=96% (at 254 nm, RT=5.097 min), m/z [positive ion]=525.2.

Having now fully described this disclosure, it will be understood by those of ordinary skill in the art that the same can be performed within a wide and equivalent range of conditions, formulations and other parameters without affecting the scope of the invention or any embodiment thereof.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and publications cited herein are fully incorporated by reference herein in their entirety.

What is claimed is:

1. A process for preparing a compound of Formula I:

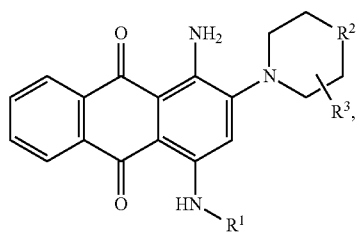

or a salt thereof,
wherein:
$R^1$ is optionally substituted aryl;
$R^2$ is NRor $CR^9R^{10}$;
$R^3$, $R^9$, and $R^{10}$ are independently selected from the group consisting of hydrogen, halogen, CN, $NH_2$, $NO_2$, $C_{1-4}$ haloalkyl, —$OC_{1-4}$ haloalkyl, $C_{1-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —O—$C_{6-10}$ aryl, —O—$C_{5-10}$heterocycle, —$C(O)CF_3$, —$(CH_2)_n$halogen, —$(CHR)_n$—O)$_n$—$C(=O)R^8$, —$(CHR)_n$—(S)$_n$—$C(=O)R^8$, —$OR^a$, —$NR^{11}R^{12}$, —$NR^aCOR^{11}$, —$NR^a$COOR$^a$, —$NR^aSO_2R$, —$NR^aCONR^{11}R^{12}$, —$COR^a$, —$(CHR)_nCOOR^a$, —S—$C_{1-6}$ alkyl, and —$CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;
$R^7$ is hydrogen, halogen, CN, $C_{1-4}$ haloalkyl, —$OC_{1-4}$ haloalkyl, $C_{1-6}$ alkyl, $C_{2-6}$ alkenyl, $C_{2-6}$ alkynyl, —$(CHR)_nC_{6-10}$ aryl, —$(CHR)_nC_{5-8}$ heterocycle, —$(CHR)_nC_{3-8}$ cycloalkyl, —$C(O)CF_3$, —$(CH_2)_n$halogen, —$COR^a$, —$(CHR)nCOOR^a$, and —$CONR^{11}R^{12}$, wherein each said alkyl, alkenyl, alkynyl, aryl, cycloalkyl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;
$R^{11}$ and $R^{12}$ are independently selected from the group consisting of hydrogen, N($R^a$)C(=O)R, halogen, CN, $NH_2$, $NHR^a$, $NO_2$, $C_{1-4}$ haloalkyl, —$OC_{1-4}$ haloalkyl, $C_{1-6}$ alkyl, $C_{2-8}$ alkenyl, —S—$C_{1-6}$alkyl, —$C(=O)$—$(O)_n$—$R^a$, —$(CHR)_n$—$(O)_n$—$C(=O)R^8$, —$(CHR)_n$—$(S)_n$—$C(=O)R^8$, —$OR^a$, —$(CHR)_nC_{3-10}$ cycloalkyl, —$(CHR)_nC_{6-10}$aryl, —$(CHR)_nC_{5-10}$ heteroaryl, and —$(CHR)_nC_{5-10}$ heterocycle, wherein each said alkyl, alkenyl, cycloalkyl, aryl, heteroaryl and heterocycle is independently optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$, and wherein one or more carbon atoms of said alkyl may be replaced with one or more heteroatoms selected from the group consisting of nitrogen, oxygen, and sulfur; alternatively, $R^{11}$ and $R^{12}$, taken together with the atom(s) to which they are attached, form a 3 to 6 membered heterocyclic group containing one or more heteroatoms independently selected from the group consisting of nitrogen, oxygen, and sulfur; wherein the heterocyclic group is optionally substituted with 1 to 2 groups independently selected from $C_{1-6}$ alkyl, halogen, CN, $NO_2$, $NH_2$, $NHR^a$, $SO_2R^{13}$, or $NR^aSO_2R^{13}$;

R each independently represents hydrogen, halogen, CN, $NO_2$, $NH_2$, or $C_{1-6}$ alkyl;

$R^a$ each independently represents hydrogen or $C_{1-6}$ alkyl;

$R^8$ each independently represents $C_{1-6}$ alkyl, halogen, CN, $NO_2$, $NH_2$, $NHR^a$, $SO_2R^{13}$, or $NR^aSO_2R^{13}$;

$R^{13}$ is hydrogen, $C_{1-6}$ alkyl, cycloalkyl, aryl, heteroaryl, or heterocycle; and n represents an integer from 0 to 3;

said process comprising reacting a compound of Formula II:

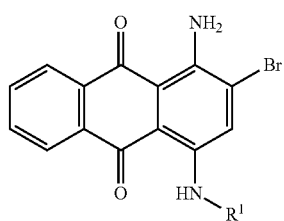

II wherein:
$R^1$ is optionally substituted aryl;
with

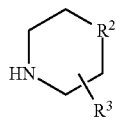

wherein:
$R^2$ and $R^3$ are defined as above;
to give said compound of Formula I.

2. The process of claim 1, wherein said reacting step is carried out in a polar, aprotic solvent.

3. The process of claim 1, wherein said reacting step takes place in the presence of a base.

4. The process of claim 3, wherein the base is triethyl amine.

5. The process of claim 1, further comprising:
subjecting the compound of Formula I or a salt thereof:

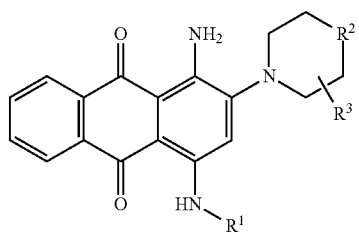

I wherein:
$R^1$, $R^2$, and $R^3$ are defined as in claim 1,
to conditions that result in an intramolecular ring closing reaction to form a compound of Formula IV:

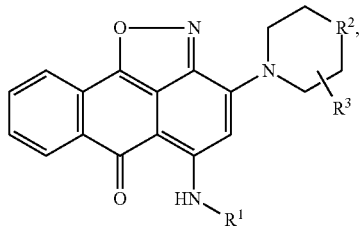

IV or a salt thereof,
wherein:
$R^1$, $R^2$, and $R^3$ are defined as in claim 1.

6. The process of claim 5, wherein said process further comprises:
reacting the compound of Formula I or a salt thereof:

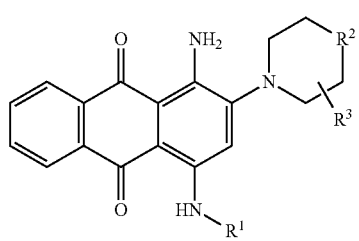

I with a nitrite in the presence of an acid to form a compound of Formula V:

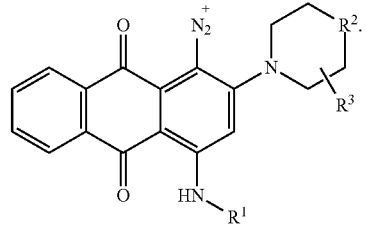

V

7. The process of claim 6, wherein in the nitrite is sodium nitrite and the acid is sulfuric acid.

8. The process of claim 6, wherein the reaction is carried out at a temperature from about 35° C. to about 75° C.

9. The process of claim 6, wherein said process further comprises:
reacting the compound of Formula V with an azide in the presence of a solvent to form a compound of Formula VI:

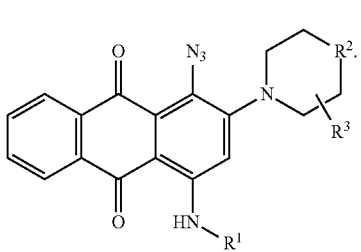

VI

10. The process of claim 9, wherein in the azide is sodium azide and the solvent is water.

11. The process of claim 9, wherein the reaction takes place in a period of time of about 6 hours to about 18 hours.

12. The process of claim 9, wherein said process further comprises:
heating the compound of Formula VI in the presence of a solvent to form a compound of Formula IV.

13. The process of claim 12, wherein the solvent is toluene.

14. The process of claim 12, wherein the reaction is carried out at a temperature from about 50° C. to about 90° C.

15. The process of claim 5, wherein said process further comprises:
1) reacting the compound of Formula I or a salt thereof:

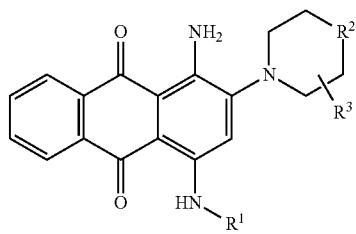

with a nitrite in the presence of an acid to form a compound of Formula V:

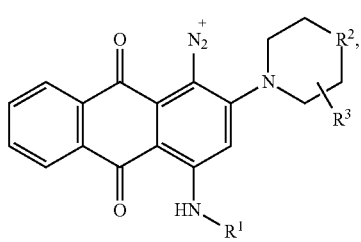

2) reacting the compound of Formula V with an azide in the presence of a solvent to form a compound of Formula VI:

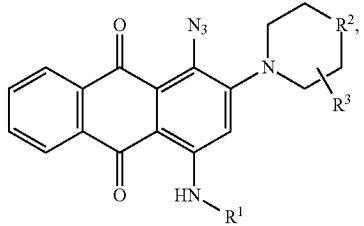

and
3) heating the compound of Formula VI in the presence of a solvent to form a compound of Formula IV.

16. The process of claim 1, further comprising reacting a compound of Formula III:

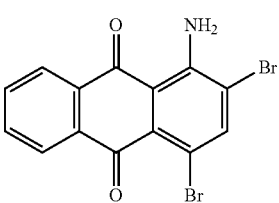

with $H_2NR^1$
wherein:
$R^1$ is optionally substituted aryl;
to give said compound of Formula II:

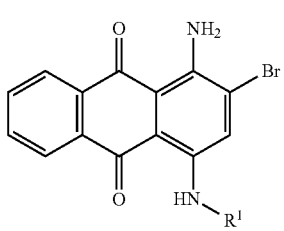

wherein:
$R^1$ is optionally substituted aryl.

17. The process of claim 16, wherein said reacting step is carried out in cyclohexyl alcohol.

18. The process of any one of claims claim 16, wherein said reacting step takes place in the presence of copper (II) acetate, copper metal, and potassium acetate.

19. The process of claim 1, wherein:
$R^1$ is

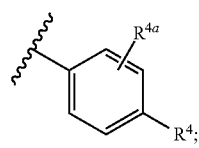

$R^4$ is COOH;
$R^{4a}$ is hydrogen;
$R^2$ is $NR^7$;
$R^3$ is H; and
$R^7$ is cyclohexyl.

* * * * *